United States Patent [19]

Brodniewicz

[11] Patent Number: 5,630,842

[45] Date of Patent: May 20, 1997

[54] BIOCOMPATIBLE SURGICAL IMPLANT

[75] Inventor: Teresa Brodniewicz, Laval, Canada

[73] Assignee: Haemacure Biotech Inc., Quebec, Canada

[21] Appl. No.: 186,590

[22] Filed: Jan. 26, 1994

Related U.S. Application Data

[63] Continuation-in-part of Ser. No. 919,252, Jul. 27, 1992, abandoned.

[51] Int. Cl.$^6$ ........................................ A61F 2/12
[52] U.S. Cl. ........................... 623/8; 623/11; 623/14; 623/15; 523/113; 424/423; 424/424; 514/1; 514/14; 530/382
[58] Field of Search ............................... 424/423, 424; 523/113; 514/1, 21; 623/8, 11, 15, 14; 530/382

[56] References Cited

U.S. PATENT DOCUMENTS

| | | | |
|---|---|---|---|
| 2,576,006 | 11/1951 | Ferry et al. | 530/382 |
| 3,933,996 | 1/1976 | Charlton et al. | 514/21 |
| 4,157,085 | 6/1979 | Austad | 623/15 |
| 4,507,810 | 4/1985 | Bartholdson | 623/8 |
| 4,647,536 | 3/1987 | Mosbach et al. | 435/177 |
| 4,648,880 | 3/1987 | Braumann | 623/8 |
| 4,822,535 | 4/1989 | Ekman et al. | 264/4.3 |
| 4,863,733 | 9/1989 | Startz et al. | 623/8 |
| 4,925,678 | 5/1990 | Ranney | 424/493 |
| 4,960,757 | 10/1990 | Kumpe et al. | 514/21 |
| 5,002,071 | 3/1991 | Harrell | 623/8 |
| 5,112,457 | 5/1992 | Marchant | 525/366 |

FOREIGN PATENT DOCUMENTS

| | | |
|---|---|---|
| 0166263 | 1/1986 | European Pat. Off. . |
| 0305243 | 3/1989 | European Pat. Off. . |
| 0485210 | 5/1992 | European Pat. Off. . |
| 1745676 | 7/1970 | Germany ........... 623/11 |

OTHER PUBLICATIONS

International Search Report (International Application No. PCT/CA93/00302, filed Jul. 27, 1993).
PCT/US85/01695, filed Sep. 4, 1985.

Primary Examiner—Andrew E. C. Merriam
Attorney, Agent, or Firm—Hoffman, Wasson & Gitler

[57] ABSTRACT

The invention provides a biocompatible surgical implant particularly useful for breast or testicular reconstruction or augmentation comprising a stabilized fibrin semisolid, optionally sealed in a shaped shell. Preferred starting material for production of the implant is whole plasma from autologous or homologous donation, concentrated with respect to fibrinogen.

23 Claims, No Drawings

BIOCOMPATIBLE SURGICAL IMPLANT

This is a continuation-in-part of application Ser. No. 07/919,252 filed on Jul. 27, 1992, now abandoned.

BACKGROUND OF THE INVENTION

1. Field of the Invention

The invention relates to biocompatible implants or prostheses for use in soft tissue remodelling, especially for cosmetic surgery or post-surgical or post-traumatic tissue reconstruction. In particular, the invention relates to a biocompatible implant for breast or testicle reconstruction or augmentation.

2. Description of Related Art

Contemporary breast implants typically comprise appropriately shaped shells or envelopes of a synthetic plastic encasing a filler material. An early filler material, physiological saline, proved to be cosmetically unsatisfactory owing to its low viscosity, and has been widely replaced by fillers comprising solids, semisolids, gels, or liquids of higher viscosity which more nearly approximate the physical properties of the human breast. Foamed rubber (U.S. Pat. No. 3,795,921); synthetic resins such as polyvinylpyrrolidone, polyisocyanate, polyvinyl alcohol, polyvinyl esters, polyamides, polyurethanes, polymerized hydrocarbons, and polyvinylchloride (U.S. Pat. Nos. 4,157,085, 4,787,905 and 5,067,965); vegetable oils such as peanut or sunflower seed oil; plasticized starch gel (U.S. Pat. No. 4,612,009); and interconnected cells (U.S. Pat. No. 4,507,810) are exemplary. However, for many years the filler material of choice for breast implants has been silicone oil or gel. While generally more cosmetically suitable than saline, these and other implant filler materials incompatible with the human body pose a definite clinical hazard if the shell containing the filler disintegrates or ruptures with leakage of the contents, a relatively common occurrence. Documented reactions of mammals exposed to exogenous implant materials include inflammation, edemas, foreign body cysts, granulomas, fibrosis, and, most recently in the case of silicone gels, autoimmune disease.

SUMMARY OF THE INVENTION

The invention provides an implant for soft tissue reconstruction or augmentation, particularly a breast or testicle implant, comprising a semisolid of crosslinked fibrin strands of the desired cosmetic characteristics for the intended application. The fibrin semisolid is conveniently obtained by coagulation of a plasma fraction enriched in fibrinogen and containing plasma factors necessary for coagulation, derived from blood preferably autologous or homologous to the implant recipient to avoid introduction of immunogenic foreign proteins into the body. For optimal results, the starting plasma fraction is substantially devoid of proteolytic enzymes or other blood components which might contribute to deterioration of the product or inhibit its production. This is accomplished by procedures known in the art.

The fibrin semisolid of the invention may be used per se as the implant, or may be molded or contoured as cosmetically desirable and/or encased in a conventional shell or envelope such as those encasing the filler materials in the above-mentioned U.S. patents for implantation, for example to inhibit any possible resorption of the implant. The product may include one or more components as desired to modify the physical or chemical characteristics of the final product.

In contrast to known implant materials such as saline the fibrin semisolid of the invention has excellent cosmetic properties, particularly contourability and flexibility combined with strength, coupled with little or no potential toxicity such as that associated with silicone gels. The product is readily tailored for the cosmetic needs of the individual recipient by varying the amounts of coagulation factors employed, and/or additives, and has the advantage of not requiring a shell or envelope inimicable to the human body as a shield against toxic reaction of the body to the implant.

DETAILED DESCRIPTION OF THE INVENTION

The stabilized fibrin semisolid of the invention is prepared under physiological conditions from an aqueous solution essentially containing solubilized fibrinogen and effective amounts of plasma factors known to be required for converting fibrinogen to a semisolid crosslinked fibrin polymer having the desired physical characteristics. The product is stabilized by removal or inactivation of any proteolytic (particularly fibrinolytic) enzymes present, or other components which might contribute to biodegradation of the product, either prior to implant or as implanted, and is preferably sterilized prior to use to inactivate or remove any potentially deleterious materials present.

As known in the art, fibrinogen, a soluble plasma protein, is readily converted in vitro in aqueous solution under physiological conditions to fibrin, an insoluble polymer. The reaction proceeds in the presence of thrombin (a proteolytic enzyme which cleaves small polypeptides from the fibrinogen molecule to produce fibrin monomer and also activates factor XIII, fibrin stabilizing factor) and factor XIII (which functions as a crosslinking agent to stabilize the resulting fibrin polymer against biodegradation), according to the following mechanism:

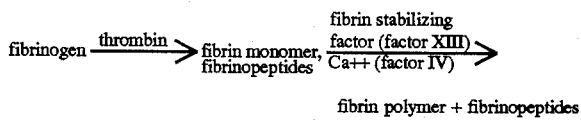

fibrin polymer + fibrinopeptides

Calcium ions, which participate in vivo, are not essential to the in vitro reaction, but contribute per se or as equivalents to the structure of the product as described below.

Under non-denaturating conditions, clottable fibrinogen is readily converted according to this mechanism to a semisolid of insoluble fibrin polymer suitable for use in the practice of the invention. In general, clottable fibrinogen is readily converted in vitro in aqueous solution under conditions of reaction comprising a pH of from about 6.5 to about 8, at room temperature and pressure; temperatures of from about 10° C. to about 40° C. are suitable, and about 20° C. is particularly recommended.

In one embodiment of the invention, to produce the stabilized crosslinked fibrin semisolid product of the invention, an aqueous polymerization solution is made up, broadly containing sufficient clottable fibrinogen (herein referred to as "fibrinogen") as measured by a standard method, such as the method of Clauss described in *Acta Haematol.* 17: 237; 1957, incorporated herein by reference) to obtain a product of the desired size. Thrombin, factor XIII, and optional cations such as calcium ions or other cocrosslinking agent for crosslinking of the polymer, are included in sufficient amounts to substantially convert the clottable fibrinogen to fibrin monomer, polymerize the monomer, and crosslink the fibrin polymer to a product of the desired physical characteristics. The fibrinogen/ thrombin/factor XIII ratio and the amount of the optional cocrosslinking agent(s) are controlled for the individual application to provide a physically stable semisolid product of the desired tensile strength, elasticity (flexibility), or other physical characteristic for the intended use. Any components present which might contribute to biodegradation of the product are removed or inactivated to the extent feasible or necessary to provide a biochemically stable semisolid product. In general, a sufficient amount of thrombin is provided to substantially monomerize clottable fibrinogen present measured as described above and to activate factor XIII present to provide a semisolid crosslinked fibrin polymer of adequate strength and structural stability for the intended use, most preferably having a flexibility approximating that of the natural tissue it is replacing or augmenting. Cocrosslinking agents such as calcium ions are included as necessary or desirable to obtain a product of the desired physical characteristics. Excessive amounts of thrombin/factor XIII/cocrosslinking agent are undesirable, as the product will toughen and lack flexibility. Conversely, insufficient amounts of thrombin/factor XIII/cocrosslinking agent are undesirable, as the product will lack cohesiveness, strength, and stability. In an exemplary embodiment, ratios of fibrinogen/thrombin for most applications are from about 2 to 150 mg fibrinogen to about 1 to 1000 IU (International Units) of thrombin, based on a factor XIII ratio of from about 0.01 to 250 units of factor XIII. The quantity of fibrinogen, thrombin, factor XIII and any cocrosslinking agent such as calcium ion is varied as described above to provide a cosmetically suitable product of a strength and flexibility adapted to individual needs.

In an exemplary embodiment, a semisolid fibrin product according to the invention useful for breast or generic implantation is characterized by sufficient deformability to provide a Precision Penetrometer reading of about 100 to 250, preferably about 180. The instrument comprises a weighted probe which is dropped from a standard height into a standardized amount of test material; deformation of the product over time is reflected by the reading obtained. The instrument is available from The Precision Scientific Petroleum Instruments Co., Bellwood, Ill. (USA). Implant characteristics may be matched by providing a product of comparable size and thickness having closely similar deformity as measured by the Precision Penetrometer or comparable instrument, with appropriate sizing and contouring.

In general, depending upon the desired physical characteristics of the product, the aqueous polymerization solution with no non-essential additives contains 1) at least about 2 mg of fibrinogen per ml of water (preferably distilled or deionized water), and preferably at least about 20 mg of fibrinogen per ml of water, up to about 150 mg fibrinogen per ml of water; 2) at least about 2 IU to about 1000 IU thrombin per ml water fibrinogen solution, or an amount sufficient to substantially polymerize available fibrin monomer; and 3) at least about 0.4 units of factor XIII per 100 mg of fibrinogen, or at least an amount sufficient to substantially stabilize the resultant polymer. The solution may also contain additives in addition to materials noted, with adjustment of the amounts of fibrinogen, thrombin, factor XIII, and any cocrosslinking agent, as necessary.

As noted above, calcium ions are not essential to the polymerization reaction; however, calcium ions or other cocrosslinking agent such as divalent alkaline earth metal cations promote crosslinking of the fibrin polymer as known in the art and preferably are added in an amount sufficient to rigidify the product to the extent desired. Suitable sources of calcium or other cations include any salts of these cations having good water-solubility wherein the anion is substantially neutral in the polymerization reaction, such as calcium chloride. Addition of calcium chloride to the above-described polymerization solution containing fibrinogen, thrombin, and factor XIII to provide an about 0.1 to 50 mM solution of $CaCl_2$ is exemplary.

The starting materials fibrinogen, thrombin, and factor XIII are readily available commercially. Human or bovine fibrinogen and thrombin suitable for use in the practice of the invention are available from Calbiochem, San Diego, Calif. (USA) and factor XIII from American Diagnostics, Inc., Greenwich, Conn., USA.

If desired, the aqueous polymerization solution, containing fibrinogen, thrombin, factor XIII and optional $Ca^{++}$ or other cocrosslinking agent also may contain, for example, solid or semisolid particulates for entrapment into the fibrin polymer as it forms for modification of the physical characteristics of the product, such as naturally-occurring proteins including collagen, albumin, or immunoglobulin; any such proteins are preferably autologous to the implant recipient to avoid immunogenic effects. The polymerization solution may also contain other additives for incorporation into the product which contribute to its physical or chemical characteristics such as bubbles of entrapped gas, e.g., nitrogen, or additives such as signal enhancers to facilitate subsequent mammography screenings in the instance of breast implant. Other additives as useful may be incorporated into the product, at any stage of the process.

In a preferred procedure, the polymerized fibrin monomer (fibrin coagulate or semisolid) of the invention is derived from whole plasma obtained by autologous or homologous donation from a human, although any suitable plasma, including that from heterologous donation, can be used as starting material. The plasma is collected into anticoagulant by customary methods and treated preferably under sterile conditions to remove plasminogen (a fibrinolytic enzyme) and concentrate fibrinogen and factor XIII. The resulting fibrinogen-enriched fraction, depleted of plasminogen, is then coagulated with thrombin and optional cocrosslinking agent to produce the stabilized fibrin polymeric semisolid of the invention.

In the best mode of the invention as presently known, human autologous or homologous plasma cryoprecipitate or ethanocryoprecipitate obtained by deep-freezing and thawing of collected plasma as known in the art is employed as starting material to produce the semisolid fibrin product of the invention. Useful standard cryoprecipitate generally mainly comprises plasma proteins fibrinogen, fibronectin, factor VIII complex, and factor XIII; albumin, plasminogen, and immunoglobulins may also be present in this fraction.

The starting cryoprecipitate is obtainable from plasma fractionation centers, or may be produced in local laboratories, particularly in the case of autologous plasma. Starting cryoprecipitate is then preferably treated to concentrate fibrinogen and factor XIII and remove plasminogen, for example by resuspension of the cryoprecipitate in plasma or buffer (e.g., Tris buffered saline comprising about 0.04M Tris and about 0.15M NaCl) followed by adsorption on lysine-Sepharose (Pharmacia, Uppsala, Sweden) to remove plasminogen. Alternatively, collected plasma may be first purified by affinity chromatography as above to remove plasminogen, and then cryoprecipitated as described above.

These or other purification procedures are repeated as necessary both to increase concentration of fibrinogen and factor XIII to provide solution concentrations of these clotting components as described above, and to substantially remove any plasma components present which would be deleterious to the polymerization of the fibrin monomer or to the product, particularly fibrinolytic or other proteolytic enzymes such as plasminogen; preferably, plasma proteins extraneous to the product such as immunoglobulins are also be removed to the extent economically feasible. Further, product fibrinogen solution obtained from whole plasma is preferably additionally stabilized prior to coagulation against enzymatic degradation of essential proteins by addition of a suitable proteolytic enzyme inhibitor such as Trasylol (Sigma Chemical, MO, USA). Broadly, for use in the practice of the invention, depending upon the application, plasma-derived purified fibrinogen solution preferably contains fibrinogen and factor XIII in the amounts described above, and is substantially devoid of active plasma components present which are deleterious to the desired implant properties, to produce a semisolid of fibrin strands stabilized against biodegradation for long-term life in the intended environment.

To coagulate, the plasma-derived purified fibrinogen solution from above is mixed with thrombin from a suitable source (e.g., bovine or human thrombin) and optionally calcium ions or other cocrosslinking agent under non-denaturating conditions. The fibrinogen rapidly coagulates or polymerizes to fibrin, forming the semisolid of fibrin strands of the invention. The coagulate is then allowed to stand for a period of time sufficient to permit customary contraction and exudation of liquid, usually for about 6 to 24 hours. Substantial complete polymerization of fibrinogen to fibrin polymer, with a high degree of crosslinkage of the polymer during preparation thereof and postcoagulation provides a highly resorption-resistant fibrin product containing only residual fibrinogen, which is particularly useful in the practice of the invention.

At any stage, product obtained by non-autologous donation is preferably treated to inactivate any viral material present, as by solvent/detergent or pasteurization methods known in the art (see, e.g., U.S. Pat. Nos. 4,540,573; 4,764,363; 4,820,805; or European Patent EP 0,131,740, incorporated herein by reference) which do not significantly affect the activity of clotting factors essential to the invention. Whatever process is employed, the entire process is preferably carried out under sterile conditions.

Fibrin product obtained by any suitable process may be employed according to the invention as implant per se or placed in an appropriately shaped envelope or shell under sterile conditions and sealed as known in the art. Any suitable biocompatible shell or envelope material such as Teflon may be used to encase the fibrin semisolid prior to implantation. The product may be molded or contoured as appropriate during any stage of the process. In order to preserve the structure of the material and ensure inactivation of any enzymes or possible viruses, the implant is preferably treated prior to use, whether or not encased in a shell, as by heat and/or irradiation. Postcoagulation stabilization with e.g., glutaraldehyde or formaldehyde is also contemplated. A recommended heat treatment comprises exposure of the product to a temperature of from about 60° C. to about 105° C. for a period of time ranging from about 1 min to about 200 hours. Irradiation is effective at dosages from about 5 to 100 kGrays.

For clinical use, the fibrin semisolid product of the invention is implanted in the body by surgical methods known in the art, for example, those conventionally employed for the surgical implant of silicone gels. As discussed above, the product is useful for soft tissue modification, particularly plastic surgery involving soft tissue reconstruction, augmentation, or the like. These uses are collectively referred to herein as "soft tissue anaplasty."

EXAMPLES

Example 1

Plasma from autologous donation is collected and submitted to affinity chromatography on a lysine-Sepharose column (Pharmacia-Uppsala, Sweden), in order to remove plasminogen. The obtained effluent is deep-frozen for at least 6 hrs. and cryoprecipitate is obtained by slow thawing of the plasma at a temperature of below 10° C. Thus obtained cryoprecipitate is harvested by centrifugation at the temperature below 10° C., washed twice with citrated saline and resuspended in Tris buffered saline at the concentration of 45 mg of fibrinogen gen/ml of the buffer. To this solution a protease inhibitor (for example, Trasylol, Sigma, Mo., U.S.A.) is added at a concentration of 10000 of KIU/ml of the product. The solution is sterile filtered and coagulated under sterile conditions by the addition of 50 I.U. of human thrombin in 50 mM $CaCl_2$.

The resulting coagulated material is submitted to incubation for a period of 6 hrs at 37° C. and heat-treated at 70° C. for a period of 100 hrs in a sealed container. After this procedure, the solid implant is taken, placed in a plastic shell and sealed according to the known technique. The obtained implant is irradiated by 80 kGrays and ready for the implantation.

Example 2

Plasma obtained from homologous donation is deep frozen for a period of 6 hrs. The plasma is thawed and warmed to a temperature of 30°. Following this the plasma is cooled to a temperature of 0° C. and precooled ethanol at a concentration of 10% is added to it. The solution is slowly mixed overnight at 0°. The next day ethanocryoprecipitate is harvested by centrifugation, washed twice with citrated buffer and resuspended in buffer containing 0.02M Tris and 0.15M NaCl pH 7.1. The solution is submitted to affinity chromatography on lysine-Sepharose in order to remove plasminogen. The resulting effluent is submitted to an antiviral treatment such as solvent/detergent (Tri-n-butyl phosphate/Tween 20) for a period of 6 hrs at 30°. Viral inactivation is followed by double reprecipitation in the cold with 10% ethanol as is described in Example 1 and by extensive washing.

The resulting precipitate is recovered, resuspended in a concentration of 60 mg of fibrinogen/ml of Tris-saline containing Trasylol (15 000 K.I.U.). The product is sterile filtered and coagulated by 20 Units of thrombin in 0.025M $CaCl_2$. The product is incubated overnight at 37° C., then sealed, and subjected to heat treatment at 80° for 72 hours and gamma irradiation of 100 kGrays. The product is implanted without incasting in a plastic shell.

Example 3

Commercial human fibrinogen (Calbiochem) is resuspended in a concentration of 55 mg of fibrinogen/ml of buffered saline, factor XIII is added in the quantity of 30 units/ml and human albumin in a concentration of 5 mg/ml. The product is submitted to viral inactivation by solvent/detergent (Tri-n-butyl-phosphate and Triton) for a period of 10 hrs at 37°; this is followed by affinity chromatography removal of residual plasminogen and solvent/detergent mixture.

The resulting solution is sterile filtered and coagulated by the addition of bovine thrombin in a concentration of 15 units/ml of the product under sterile conditions. The product is incubated at 30° for 10 hrs and then heated at 70° C. for a period of 100 hrs. The excluded solution is removed and the product, after incasting in a plastic shell, is submitted to 90 kGrays of gamma irradiation. The thus-obtained product is ready for implantation.

What is claimed is:

1. A surgical prosthesis for soft tissue reconstruction or augmentation in a mammal comprising a resorption-resistant semisolid fibrin coagulate consisting essentially of insoluble fibrin polymer strands stabilized against biodegradation and sealed in a biocompatible, resorption-resistant plastic shell, wherein the semisolid fibrin coagulate is produced from a fibrinogen solution consisting essentially of fibrinogen, thrombin, and factor XIII in amounts sufficient to substantially convert the fibrinogen to insoluble fibrin polymer.

2. The prosthesis of claim 1, wherein the semisolid fibrin coagulate is produced from a plasma fraction consisting essentially of fibrinogen, thrombin, and factor XIII in amounts sufficient to substantially convert the fibrinogen to insoluble fibrin polymer.

3. The prosthesis of claim 1, wherein the fibrinogen solution further includes a cocrosslinking agent.

4. The surgical prosthesis of claim 2, wherein the plasma fraction further includes a cocrosslinking agent.

5. The surgical prosthesis of claim 1, wherein the fibrinogen solution contains from about 1 to 1000 IU thrombin per about 2 to 150 mg fibrinogen, and about 0.01 to 250 units factor XIII per about 1 gm fibrinogen.

6. The surgical prosthesis of claim 2, wherein the plasma fraction contains from about 1 to 1000 IU thrombin per about 2 to 150 mg fibrinogen, and about 0.01 to 250 units factor XIII per about 1 gm fibrinogen.

7. The surgical prosthesis of claim 3, wherein the cocrosslinking agent is calcium chloride present in the fibrinogen solution in a concentration of about 0.001 to about 50 mM.

8. The surgical prosthesis of claim 4, wherein the cocrosslinking agent is calcium chloride present in the plasma fraction in a concentration of about 0.001 to about 50 mM.

9. The surgical prosthesis of claim 4, wherein the plasma fraction is substantially free of biologically active proteolytic enzymes.

10. The surgical prosthesis of claim 9, wherein the coagulate is stabilized by treatment with a crosslinking agent.

11. The surgical prosthesis of claim 2, stabilized against biodegradation by substantial removal of plasma components deleterious to the stability of the product from the plasma fraction; deactivation of proteolytic enzymes present; and crosslinkage of the fibrin polymer.

12. The surgical prosthesis of claim 2, wherein the plasma is autologous or homologous to the mammal.

13. The surgical prosthesis of claim 6, wherein the plasma is autologous or homologous to the mammal.

14. The surgical prosthesis of claim 1, wherein the prosthesis is a breast or testicle prosthesis.

15. The surgical prosthesis of claim 2, wherein the prosthesis is a breast or testicle prosthesis.

16. The surgical prosthesis of claim 2, wherein the prosthesis is a breast prosthesis and wherein the plasma is autologous to the mammal.

17. The prosthesis of claim 1, implanted in the soft tissue of a mammal.

18. A method for soft tissue anaplasty in a mammal comprising surgically implanting the prosthesis of claim 1 in the mammal.

19. A method for soft tissue anaplasty in a mammal comprising surgically implanting the prosthesis of claim 2 in the mammal.

20. A method for soft tissue anaplasty in a mammal, comprising surgically implanting the prosthesis of claim 15 in the mammal.

21. A method for mammaplasty in a mammal, comprising surgically implanting the prosthesis of claim 16 in the breast of the mammal.

22. The surgical prosthesis of claim 1, having a deformability corresponding to a Precision Penetrometer reading of about 180.

23. The surgical prosthesis of claim 2, having a deformability corresponding to a Precision Penetrometer reading of about 180.

* * * * *